United States Patent [19]

Ferro

[11] Patent Number: 4,999,341

[45] Date of Patent: Mar. 12, 1991

[54] APPETITE MODERATING AND ANTI-GASTRITIS COMPOSITION

[76] Inventor: Antonio Ferro, Via Maraini 7, 6900 Lugano (Svizzera), Italy

[21] Appl. No.: 414,738

[22] Filed: Sep. 27, 1989

Related U.S. Application Data

[63] Continuation of Ser. No. 243,192, Sep. 8, 1988, abandoned, which is a continuation of Ser. No. 909,930, Sep. 22, 1986, abandoned.

[30] Foreign Application Priority Data

Sep. 26, 1985 [IT] Italy ................. 22284 A/85

[51] Int. Cl.$^5$ ................. A61K 31/70; A61K 31/73
[52] U.S. Cl. ................. 514/33; 514/26; 514/909; 536/18.1; 536/20; 536/5; 424/451; 424/464
[58] Field of Search ............ 536/18.1, 20, 55.2, 536/5; 514/33, 55, 909, 26; 424/464, 451

[56] References Cited

U.S. PATENT DOCUMENTS

| | | | |
|---|---|---|---|
| 3,155,575 | 11/1964 | Doczi et al. | 536/20 |
| 3,257,275 | 6/1966 | Weisberg et al. | 514/55 |
| 4,223,023 | 9/1980 | Furda | 514/55 |
| 4,335,113 | 6/1982 | Combier et al. | 536/18.1 |
| 4,363,801 | 12/1982 | Nagyvary | 514/55 |
| 4,520,017 | 5/1985 | Tunc | 536/1.1 |
| 4,524,067 | 6/1985 | Arichi et al. | 536/18.1 |
| 4,568,667 | 2/1986 | Shirakawa et al. | 514/60 |

FOREIGN PATENT DOCUMENTS

| | | | |
|---|---|---|---|
| 3040246 | 5/1981 | Fed. Rep. of Germany | 514/33 |
| 59-55895 | 3/1984 | Japan | 536/18.1 |
| 59-70698 | 4/1984 | Japan | 536/18.1 |
| 2092445 | 8/1982 | United Kingdom | 514/33 |

OTHER PUBLICATIONS

Knorr; J. Food Science 47:593–595 (1982).

Primary Examiner—Ronald W. Griffin
Assistant Examiner—Nancy S. Carson
Attorney, Agent, or Firm—Bryan, Levitin, Franzino & Rosenberg

[57] ABSTRACT

The association of chitin or chitosan with soy saponins in an orally administered composition has appetite moderating and antigastritis activity. The objectionable side effects of the two active ingredients are also eliminated in the composition.

5 Claims, No Drawings 4,999,341

APPETITE MODERATING AND ANTI-GASTRITIS COMPOSITION

This application is a continuation of application Ser. No. 243,192 filed Sept. 8, 1988, now abandoned, which is a continuation of application Ser. No. 909,930 filed Sept. 22, 1986, now abandoned.

FIELD AND BACKGROUND OF THE INVENTION

The present invention relates to a composition which can be administered orally, and which has appetite moderating and anti-gastritis activity.

It is known that obesity and hyperphagia are both social and pathological problems. It is also known that the main drawback of currently available diets is that they do not work effectively on patients with excessive appetites. The constant feeling of hunger in such patients disturbs all of their daily activities.

People suffering from appetite disorders are also often subjected to pyrosis or gastric burning (heartburn) and a sensation of acidity in their stomachs when not eating.

SUMMARY OF THE INVENTION

The main purpose of the present invention is to provide a composition which can be administered orally and which advantageously solves the above-identified problems.

The composition of the present invention has appetite moderating and anti-gastritis activity. The composition comprises an aminopolysaccharide and a soy saponin, the aminopolysaccharide being selected from the group including chitin, chitosan and their pharmaceutically and dietetically acceptable salts.

The influence of chitin and chitosan on nutrition is known. Chitosan is extracted from some fungi and yeasts (see U.S. Pat. No. 4,363,801) or is prepared by direct deacetylation of chitin, which forms the exoskeleton of arthropods, namely the mechanical supporting tissue of the body structure of this animal class.

Chitin and chitosan are biopolymers similar to cellulose. They may be compared in structure and properties to vegetable bran, but have some other advantages which are derived from their polycationic structure (Dietrich Knorr "Functional Properties of Chitin and Chitosan" Journal of Food Science, 47, 593–595, 1982).

U.S. Pat. No. 4,363,801 also discloses some examples of salts of chitosan with acetic, citric, formic and tartaric acid, as well as with diluted mineral acids. A number of chitosan salts are known and described in the literature. These salts generally show good solubility in water.

Another known fact is that vegetable cellulose cannot be degraded by human gastric juices. Before being expelled with the feces however, vegetable cellulose does have some effects of interest regarding assimilation and indirectly regarding the lipidic condition of the feces.

From a chemical standpoint, both chitin and chitosan consist of polymerized DL-glucosamine which is insoluble in water and in most of the commonly known organic solvents. Chitosan is soluble in acidic water due to the possibility of salifying the free —$NH_2$ groups in the compound.

The main activity of these aminopolysaccharides is their capability for complexing with lipids through bonds which can be attributed to the density of their positive charges. Due to their indigestibility, lipid absorption is thus reduced. Such a property yields remarkable results in the treatment of hyperlipemia and hypercholesterolemia.

A problem with the administration of chitin or of chitosan, however, is that they both induce constipation which has self evident drawbacks. This imposes a time limitation on any treatment with chitin or chitosan, or requires recourse to auxiliary drugs.

There has also been interest on the effects of soy saponins on some particularly important biological functions. These effects, which have been found both in animal and human subjects are particularly interesting in view of the negligible toxicity of soy saponins which, however, belong to a class of substances that are generally known as being toxic (hemolytic). See H. Ohminami, T. Hayashi, Y. Kimura, E. Okuda and S. Arichi, "Effect of Soyasaponins on Hemolysis and Acute Toxicity", 2nd Department of Medical Biochemistry, School of Medicine, Ehime University, The Research Institute of Oriental Medicine, Kinki University.

Soy contains several types of saponins having the following structure:

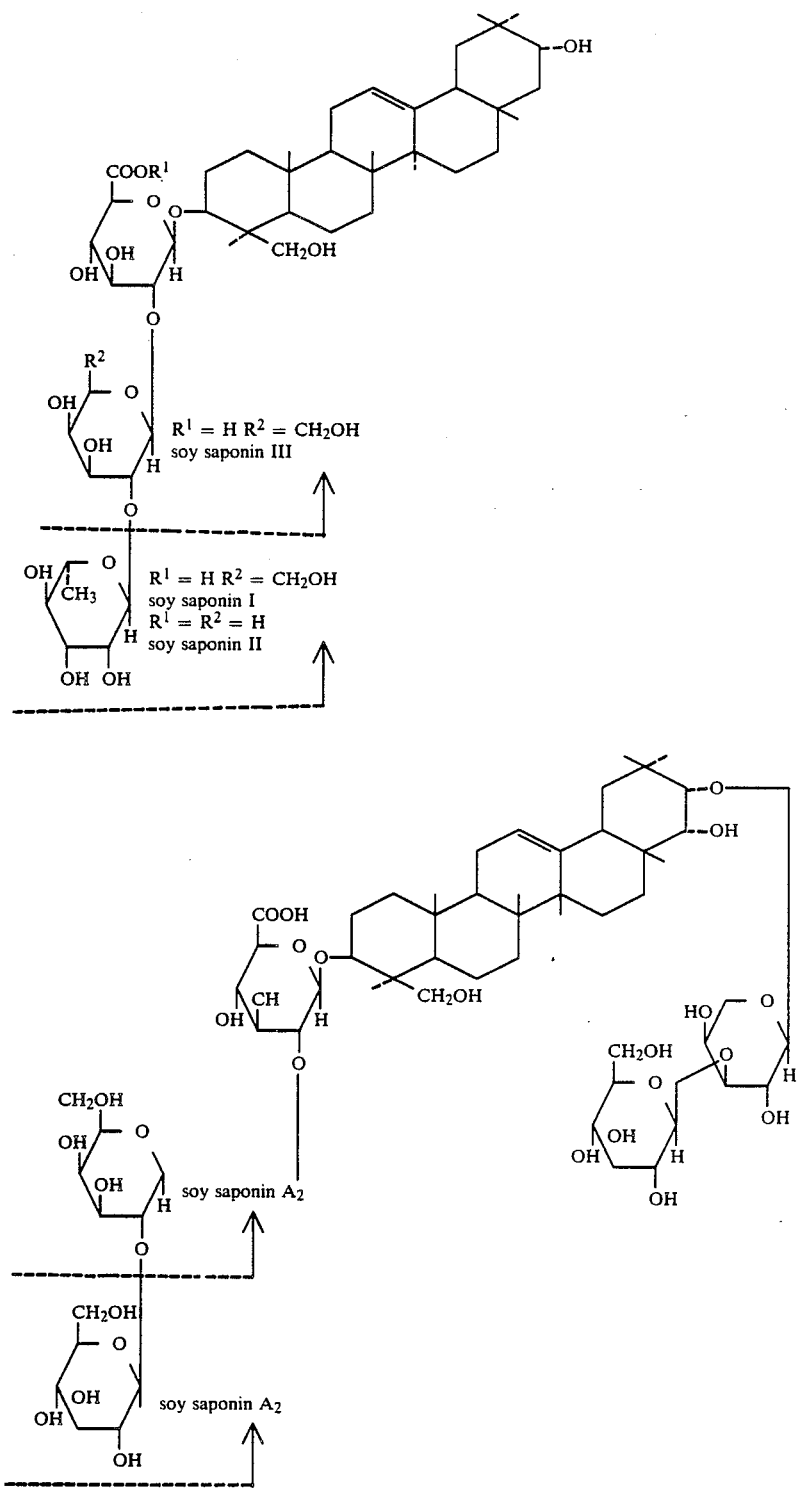

Soy saponins are essentially endowed with the following activities: lipoperoxidasic (by removing the residues of lipoperoxides which are known for damaging tissues); hepatoprotective; plateletantiaggregating; and antilipemic.

Soy saponins also have a very serious drawback, however, namely that of very easily inducing diarrhea.

Lastly, a further problem related to the known uses of chitin, chitosan and soy saponins in daily dosages which are sufficient to cause satisfactory results, is the consequent discomfort to patients taking these dosages.

SUMMARY OF THE INVENTION

According to the present invention, it has been surprisingly found that by associating the aminopolysaccharides with the soy saponins, the same activities occur at lower dosages, and moreover, the composition has other novel properties as well. Further, some secondary effects, such as the compaction (constipation) induced by chitosan and chitin, and the diarrhea sometimes attributable to the soy saponins, are entirely eliminated.

The previously known daily dosages of chitin and chitosan needed to achieve the desired effects, were between 10 and 25 grams. For the soy saponins the dosages were between 100 and 200 milligrams.

By combining the substances in a proper ratio, the dosages of the individual ingredients can be reduced by 5 to 10 times, whereby the administration dosage of the aminopolysaccharide is reduced to between 2 and 5 grams and that of the soy saponins is reduced to between 5 and 80 milligrams. The resulting advantages are evident.

While it is difficult to ingest 10, 20, or more grams of a drug daily, the reduced amounts needed according to the present invention may be in the form of tablets or other forms which are much easier and more practical to take.

The preferred ratio is thus 400 to 1000 parts by weight of the aminopolysaccharide and 1 to 16 parts by weight of the soy saponin.

The advantages of the invention appear to be attributable to a greater mutual availability of the two active ingredients, in their combination. In fact the soy saponins have surface activating properties, whereby the biolopymers are more readily dispersed. In particular, chitosan more readily forms gels with gastric liquids in the presence of the soy saponins. In vitro, for example, the gelification rate of chitosan in gastric juice is about 3 times higher if soy saponins are present. Moreover the thus formed gel is more dense and more viscous, even with the concentration of chitosan being the same.

It has been furthermore observed that the oily emulsions formed with saponins are more stable in the presence of chitin or chitosan, not only because of the thickening of the menstrua but mainly because the emulsifying action of the soy saponins is enhanced by the aminopolysaccharides.

The association of chitin or chitosan with soy saponins is endowed with the following activities: antihyperlipemic; anticholesterolemic; lipoperoxidasic; hepatoprotective; limiting liquid absorption; and moreover appetite moderating; and antigastritic.

The last two activities characterize the association of the ingredients and were never described before, for the single ingredients. Without any secondary effects, such as compaction or diarrhea, and without any sign of intolerability even in the case of extended treatments, the association between aminopolysaccharides and saponins, owing to the peculiar lipid complexing property of the composition, can be used as a slimming composition, even if the same amount of calories is ingested. Due to the capability of the composition for complexinq and rendering indigestible part of the food lipids which are ingested, the calories ingested in alimentary form are made unavailable to the organism.

Such an association has all the advantages of dietetic vegetable fibers and can also, from a chemical standpoint, be defined as an animal bran with all the advantages of a true bran. Moreover the composition has the property of complexing with fats, which is typical of aminopolysaccharidic structures which have been made surface active.

By having recourse to suitable dosages, a negative caloric balance can be obtained in the case of obesity and hyperphagia. Moreover, the appetite moderating effect of the invention also eliminates the discomfort resulting from typical hunger sensations. The gastroprotective action of the invention furthermore prevents pyrosis and burning sensations, as well as the acid sensation often reported by patients suffering from dysphagia and having disorderly alimentation.

Examples of the invention are as follows:

| Example 1-Tablets | |
| --- | --- |
| chitosan | 700 mg |
| soy saponins | 16 mg |
| lactose | 25 mg |
| magnesium stearate | 10 mg |
| Example 2-Tablets | |
| chitin | 600 mg |
| soy saponins | 10 mg |
| lactose | 50 mg |
| stearic acid | 6 mg |
| Example 3-Tablets | |
| chitosan | 550 mg |
| soy saponins | 10 mg |
| bicalcium phosphate | 100 mg |
| polyglycol 6000 | 20 mg |
| Example 4-Tablets | |
| chitosan | 350 mg |
| soy saponins | 5 mg |
| talc | 15 mg |
| Example 5-Tablets | |
| chitin | 400 mg |
| soy saponins | 15 mg |
| starch | 20 mg |
| Example 6-Oral Gel | |
| chitosan | 10.0% |
| soy saponins | 0.5% |
| citric acid | 10.0% |
| preservative and flavoring additives | enough |
| water | up to 100% |
| Example 7-Oral Gel | |
| chitosan | 12.0% |
| soy saponins | 0.2% |
| hydrogen chloride | 5.0% |
| preservative and flavoring additives | enough |
| water | up to 100% |
| Example 8 Oral gel | |
| chitosan | 8.0% |
| soy saponins | 0.3% |
| maleic acid | 7.0% |
| ethanol | 15.0% |
| preservative and flavoring additives | enough |
| water | up to 100% |

In the above description, reference has always been made to chitin and to chitosan. Their pharmaceutically and dietetically acceptable salts may also be used however. In this case, the dosages should take it into account the different molecular weight or, in other words, should be referred to the respective active compound.

Lastly it is to be pointed out that by soy saponins in the above examples the commercially available products are referred to which are normally mixtures of the several soy saponins.

What is claimed is:

1. An oral composition comprising:
   from 400 to 1000 parts by weight aminopolysaccharide selected from the group consisting of chitin, chitosan and pharmaceutically acceptable salts thereof; and
   from 1 to 16 parts by weight soy saponin.

2. An oral composition according to claim 1 comprising a daily dosage including from 2 to 5 grams of the aminopolysaccharide and from 5 to 80 milligrams of the soy saponin.

3. An oral composition according to claim 1 comprising a tablet containing from 350 to 700 milligrams of the aminopolysaccharide, from 5 to 16 milligrams of the soy saponin, at least one excipient and at least one vehicle.

4. An oral composition according to claim 1 comprising a capsule containing from 350 to 700 milligrams of the aminopolysaccharide, from 5 to 16 milligrams of the soy saponin, at least one excipient and at least one vehicle.

5. An oral composition according to claim 1 comprising a gel containing from 8 to 12% by weight of the aminopolysaccharide, from 0.2 to 0.5% by weight of the soy saponin, at least one excipient and at least one vehicle.

* * * * *